(12) United States Patent
Krammer et al.

(10) Patent No.: US 9,386,787 B2
(45) Date of Patent: Jul. 12, 2016

(54) PREPARATIONS FOR ORAL CONSUMPTION

(71) Applicant: Symrise AG, Holzminden (DE)

(72) Inventors: Gerhard Krammer, Holzminden (DE); Jakob Ley, Holzminden (DE); Katja Obst, Holzminden (DE); Katharina Reichelt, Holzminden (DE)

(73) Assignee: Symrise AG, Holzminden (DE)

( * ) Notice: Subject to any disclaimer, the term of this patent is extended or adjusted under 35 U.S.C. 154(b) by 110 days.

(21) Appl. No.: 14/074,221

(22) Filed: Nov. 7, 2013

(65) Prior Publication Data

US 2014/0134114 A1    May 15, 2014

(30) Foreign Application Priority Data

Nov. 12, 2012   (EP) ..................... 12192171

(51) Int. Cl.
| A23L 27/20 | (2016.01) |
| A23L 27/00 | (2016.01) |
| A23L 13/40 | (2016.01) |
| A61K 8/37 | (2006.01) |
| A61Q 11/00 | (2006.01) |
| A23L 1/22 | (2006.01) |
| A23L 2/56 | (2006.01) |
| A23L 1/226 | (2006.01) |
| A23F 3/16 | (2006.01) |
| C12G 3/06 | (2006.01) |
| A23L 1/314 | (2006.01) |
| A23L 1/32 | (2006.01) |

(52) U.S. Cl.
CPC ............ *A23L 1/22075* (2013.01); *A23F 3/163* (2013.01); *A23L 1/2265* (2013.01); *A23L 1/22083* (2013.01); *A23L 1/314* (2013.01); *A23L 1/3212* (2013.01); *A23L 2/56* (2013.01); *A61K 8/37* (2013.01); *A61Q 11/00* (2013.01); *C12G 3/06* (2013.01)

(58) Field of Classification Search
None
See application file for complete search history.

(56) References Cited

U.S. PATENT DOCUMENTS

| 2007/0178123 A1* | 8/2007 | Levenson ............. A61K 9/0053 424/400 |
| 2012/0196018 A1 | 8/2012 | Villagran et al. |

FOREIGN PATENT DOCUMENTS

| DE | 102010049708 A1 | 5/2012 | |
| WO | 9407477 A1 | 4/1994 | |
| WO | WO 2011012671 A1 * | 2/2011 | .............. A23L 1/015 |

OTHER PUBLICATIONS

Kerry Saretsky. The Secret Ingredient (Vanilla): Sweet Vanilla Iced Tea. Dated Jan. 9, 2011. Downloaded Sep. 29, 2015 from the site: http://www.seriouseats.com/recipes/2011/01/the-secret-ingredient-vanilla-sweet-vani.html.*
Li, Ping, et al. "Separation of tea polyphenol from green tea leaves by a combined CATUFM-adsorption resin process." Journal of food engineering 67.3 (2005): 253-260.*

* cited by examiner

*Primary Examiner* — Frederick Krass
*Assistant Examiner* — Michael P Cohen
(74) *Attorney, Agent, or Firm* — Dilworth & Barrese, LLP

(57) ABSTRACT

Preparations for oral consumption are proposed, comprising (a) lactic acid 1-menthyl ester of the general formula (I)

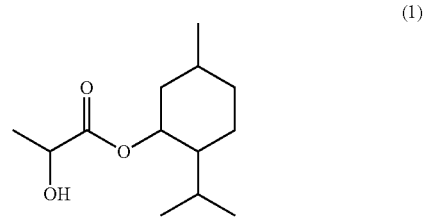

(1)

its stereoisomers or mixtures thereof,
(b) at least one substance having a bitter, astringent and/or metallic taste impression, and optionally
(c) further flavorings.

11 Claims, No Drawings

PREPARATIONS FOR ORAL CONSUMPTION

FIELD OF THE INVENTION

The field of the invention is flavourings, and it relates to the use of particular lactic acid esters for masking unpleasant taste notes.

PRIOR ART

Foodstuffs and luxury foods frequently contain a large number of different bitter substances which, despite on the one hand being desirable to a certain degree in some foodstuffs and contributing to their characteristic taste (e.g. caffeine in tea or coffee, quinine in so-called bitter lemon drinks, bitter substances from hops in beer), on the other hand can also greatly reduce the quality. Such substances include, for example, flavonoid glycosides and limonoids in citrus juices, the bitter aftertaste of many high-intensity sweeteners such as aspartame, cyclamate, acesulfame K, rebaudioside A, glycyrrhizinic acid or saccharin, and the unpleasant taste which hydrophobic amino acids and peptides can cause in cheese.

Bitter taste is generally caused by individual substances which bind to particular bitter taste receptors on taste cells which are to be found in the so-called taste buds on the tongue, and send a signal to the brain, via neurochemical cascades, which causes a defensive reaction and a negative taste impression (see Meyerhof, Reviews of Physiology, Biochemistry and Pharmacology 2005, 154, 37-72).

An astringent taste is generally caused by precipitation of proline-rich proteins in the saliva by astringents, for example metal salts, polyphenols such as (gallo)catechins, proanthocyanidins, other flavonoids or tannins. The homogeneous saliva, which normally serves as a "lubricant", then contains denatured proteins, which reduce the sliding ability and thereby leave in the mouth a rough or dry feel, which is also perceived as astringent (see Am. J. Clin. Nutr. 2005, 81, 3305-3355).

In order in particular to lower the natural content of astringents, a subsequent treatment is accordingly often necessary, for example by a preinfusion to remove catechins in the case of green tea, which preinfusion is to be discarded, or enzymatically, for example the treatment of tea with degrading enzymes in order to destroy the astringent polyphenols, as described in WO 2003 022065 A1 (Unicafe) or JP 2007 135481 A1 (Kikkoman), or the use of special peptidases in the ripening of cheese.

These treatments to lower the natural content of astringents adversely affect the product, produce waste and, for example, also give rise to solvent remains and other residues (enzymes) in the products.

It is therefore desirable to find substances which, in very small concentrations, can effectively suppress, or at least reduce, unpleasant taste impressions, in particular astringent, dry, floury, dusty, chalky and/or metallic taste impressions.

The suppression of unpleasant taste impressions is also particularly important in the case of many pharmaceutical active ingredients, because the willingness of patients, in particular children, orally to consume the preparation containing the active ingredient can thereby be increased significantly. Many pharmaceutical active ingredients, for example aspirin, salicin, paracetamol, ambroxol or quinine, to name only a very small selection for the purpose of illustration, have a pronounced astringent and/or metallic taste and/or aftertaste.

Conventionally, fat emulsions are used as counter-agents for astringents, but their use is not indicated in many cases, for example in fat-free drinks or health-conscious low-fat products.

JP 2000 287630 A1 (Shiga) and WO 2006 103930 A1 (Suntory) describe a method for reducing the astringent taste of polyphenols in tea drinks using sugar and specific amino acids. The amino acids are thereby used in the range of from 0.04 to 0.1%.

In JP 2001 046037 A1 (Kikkoman), reduction of the astringent taste of polyphenols is achieved with starch and proteins. However, this process has the disadvantage that proteins and starches in particular have a major influence on the rheological properties of the products.

In JP 2003 128664 A1 (Nagaoka), the astringency is reduced by the formation of salts of the polyphenols. Unfortunately, the stability of these compounds is reduced in many cases and the susceptibility thereof to oxidation is increased.

In JP 2004 315 441 A1 (Taisho) it is described that the astringent taste of iron salts can be reduced with particular amino acids such as γ-aminobutyric acid. However, owing to the necessary use of extremely high concentrations (1% and more), the product or preparation acquires an acidic taste.

Particular sugars such as palatinose, also in combination with sweeteners, were proposed in WO 2004 062385 A1 (Mitsui) for masking the astringency of soy drinks, but very large amounts are required here too. In WO 2005 016031 A1 (Cargill), non-reducing disaccharides such as trehalose are proposed as astringency-masking agents. JP 2004 337132 A1 (Mitsui) describes masking with cyclofructans, which mask the astringent substances by complexing. According to JP 2005 145933 A1 (Taiyo), relatively large concentrations (>0.1%) of pectin or alginates are likewise capable of reducing the astringency of polyphenols, for example from grape seed extracts. Gallate catechins, such as occur, for example, in green tea, have likewise been masked by that method (see N. Hayashi et al. in: Biosci. Biotechnol. Biochem. 2005, 69 (7), 1306-1310).

In EP 2058297 (Symrise) describes the use of unsaturated alkamides such as, for example, pellitorine or mixtures of such unsaturated aliphatic alkamides such as spilanthol and pellitorine for reducing the astringent properties of orally consumable preparations; however, because of the effective concentration that is required, the trigeminal effect, in particular the trigeminal effect described as "tingling", is also very pronounced and can interfere with the use for masking astringency.

DE 102010049708 A1 (Hexal) describes the use of mixtures comprising specific monocyclic monoterpenes (1-(2,6,6-trimethylcyclohexenyl)-2-buten-1-one, N-ethyl-2-(isopropyl)-5-methyl-cyclohexanecarboxamide, menthyl lactate, menthol ethylene glycol carbonate and menthol propylene glycol carbonate), inorganic or organic salts and also one or more sweeteners for masking bitter-tasting medicaments (e.g. cetrizidine, in a pharmaceutical film formulation. However, owing to the high dosage of the monoterpenes, which also cause a physiological cooling action, of from 0.01 to 10%, a pronounced cooling action is perceived, which interferes with the desired use as a masking agent in foodstuffs.

In some cases, sweeteners are also used to reduce astringency, as described, for example, in JP 2007 135481 A1 (Kikkoman). However, in principle only sweet applications are thereby obtained.

In addition to the disadvantages already mentioned, the above-mentioned known processes generally also have a further disadvantage in that the masking agents are to be used in considerable amounts (>0.05% range), which leads to higher costs and, in the case of polymeric carbohydrates or proteins, also to application problems.

The complex object underlying the present invention was, therefore, to find substances which, simultaneously, are suitable in very small amounts for masking or reducing the unpleasant taste impression of unpleasant-tasting substances and exhibit in particular an astringency-masking effect against a large number of astringents, are widely usable and readily available and, ideally, occur naturally.

DESCRIPTION OF THE INVENTION

The invention provides preparations for oral consumption, comprising (a) lactic acid 1-menthyl ester of the general formula (I)

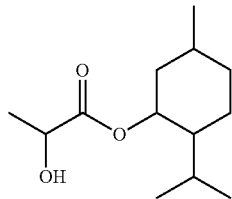

(1)

its stereoisomers or mixtures thereof, (b) at least one substance having a bitter, astringent and/or metallic taste impression, and optionally (c) further flavourings.

Surprisingly, it has been found that all of the above-mentioned lactic acid menthyl esters are particularly suitable for changing, in particular masking or reducing, an unpleasant taste or aftertaste of an unpleasant-tasting, in particular astringent, substance or substance mixture. Unpleasant taste impressions of the dry, dusty, floury, chalky or metallic type are likewise masked or reduced. It is particularly surprising that the concentration of the lactic acid menthyl esters that is required for the masking according to the invention is generally below the concentration at which the compounds of formula (1) cause a perceptible physiological cooling effect.

Lactic Acid 1-Menthyl Esters

For the purpose of clarity, the preferred lactic acid 1-menthyl esters and their possible stereoisomers are shown again in the following diagram as formulae (1-LL), (1-LD), (1-DL) and (1-DD):

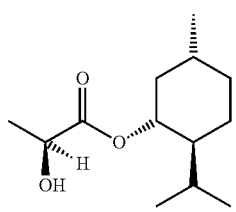

1-LL

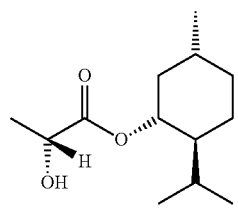

1-DL

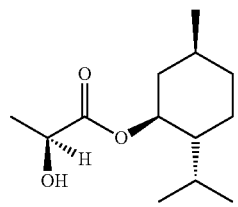

1-LD

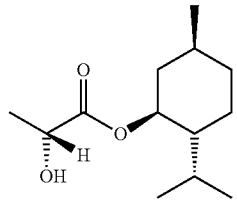

1-DD

Particular preference is given to L-lactic acid L-menthyl ester of formula (1-LL) and D-lactic acid L-menthyl ester of formula (1-DL) as individual compounds in an arbitrary mixture, particularly preferably in a mixture with more than 50 wt. %, particularly preferably more than 75 wt. %, most particularly preferably more than 95 wt. %, L-lactic acid L-menthyl ester of formula (1-LL), based on the total mass of lactic acid menthyl esters of formula (1).

These particularly preferred mixtures of the lactic acid menthyl esters of formulae (1-LL) and (1-DL) are also to be found in nature (see Gassenmeier, Flavour and Fragrance Journal 2006, 21, (4), 725-730).

Particular preference is given, therefore, to above-defined mixtures of the lactic acid menthyl esters of formula (1-LL) and (1-DL) that occur naturally or have been isolated by physical separation processes or prepared naturally by enzymatic, fermentative or conventional processes of foodstuffs production; these mixtures can be obtained from ethereal oils of the mentha family, optionally after fermentation with lactic acid bacteria or by natural esterification of natural lactic acid with natural L-menthol.

Substances Having Unpleasant Taste Impressions

The above-mentioned unpleasant-tasting substances that form component (b) can possess further, not unpleasant taste and/or odour qualities. Within the context of this text, there may be mentioned as not unpleasant taste qualities preferably the impressions spicy, umami, sweet, salty, sour, pungent, cooling, warming, burning or tingling.

Examples of substances having unpleasant taste properties that form component (b) are, for example, the following:

catechins and proanthocyanidins in a total amount of, for example, at least 0.01 wt. %, preferably of at least 0.05 wt. %, more preferably in the range of from 0.075 wt. % to 1 wt. %, caffeine and theobromine in a total amount of, for example, at least 0.005 wt. %, preferably of at least 0.01 wt. %, more preferably of at least 0.02 wt. %, yet more preferably in the range of from 0.025 wt. % to 1 wt. %, naringin in a concentration of, for example, at least 0.005 wt. %, preferably of at least 0.01 wt. %, more preferably in the range of from 0.02 wt. % to 0.5 wt. %, sweeteners in a total amount of, for example, at least 0.005 wt. %, preferably of at least 0.05 wt. %, more preferably in the range of from 0.1 wt. % to 2 wt. %, in each case based on the total weight of the preparation.

Substances that taste bitter, astringent, doughy, chalky, dusty, dry, floury, rancid and/or metallic are, for example: xanthine alkaloids, xanthines (caffeine, theobromine, theophylline), alkaloids (quinine, brucine, strychnine, nicotine), phenolic glycosides (e.g. salicin, arbutin), flavonoid glycosides (e.g. neohesperidin, eriocitrin, neoeriocitrin, narirutin, hesperidin, naringin), chalcones or chalcone glycosides, dihydrochalcone glycosides (phloridzin, trilobatin), hydrolysable tannins (gallic or elagic acid esters of carbohydrates, e.g. pentagalloyl glucose), non-hydrolysable tannins (optionally galloylated catechins or epicatechins and oligomers thereof, e.g. proanthocyanidins or procyanidins, thearubigenin), flavones and glycosides thereof (e.g. quercetin, quercitrin, rutin, taxifolin, myricetin, myrictrin), other polyphenols (γ-oryzanol, caffeic acid or esters thereof), terpenoid bitter substances (e.g. limonoids such as limonin or nomilin from citrus fruits, lupolones and humolones from hops, iridoids, secoiridoids), absinthe from wormwood, amarogentin from gentian, metal salts (potassium chloride, sodium sulfate, magnesium salts, iron salts, aluminium salts, zinc salts), pharmaceutical active ingredients (e.g. fluoroquinolone antibiotics, paracetamol, aspirin, β-lactam antibiotics, ambroxol, propylthiouracil [PROP], guaifenesin), vitamins (for example vitamin H, B-group vitamins such as vitamin B1, B2, B6, B12, niacin, pantothenic acid), denatonium benzoate or other denatonium salts, sucralose octaacetate, urea, unsaturated fatty acids, in particular unsaturated fatty acids in emulsions, amino acids (e.g. leucine, isoleucine, valine, tryptophan, proline, histidine, tyrosine, lysine or phenylalanine), peptides (in particular peptides having an amino acid from the group leucine, isoleucine, valine, tryptophan, proline or phenylalanine at the N or C terminus). The above-mentioned substances can occur either individually or in the form of a mixture, preferably also in the form of natural extracts from fresh, dried, roasted and/or fermented plants or plant parts, for example in the form of extracts from leaves, fruits, branches, roots, fruit skins, kernels, seeds, for example from *Camellia sinensis, Camellia japonica, Coffea* ssp., *Cocoa theobroma, Vitis vinifera, Citrus* ssp. and hybrids, *Poncirus* ssp. and hybrids, *Perilla, Humulus lupulus*, or related species.

Bitter substances that are to be masked according to the invention are in particular xanthines (in particular caffeine, theobromine, theophylline), phenolic glycosides (in particular salicin, arbutin), flavonoid glycosides (in particular neohesperidin, eriocitrin, neoeriocitrin, narirutin, hesperidin, naringin), chalcones or chalcone glycosides, dihydrochalcone glycosides (in particular phloridzin, trilobatin), hydrolysable tannins (in particular gallic or ellagic acid esters of carbohydrates, e.g. pentagalloyl glucose), non-hydrolysable tannins (in particular galloylated catechins or epicatechins and oligomers thereof, e.g. proanthocyanidins or procyanidins, thearubigenin), flavones and glycosides thereof (in particular quercetin, quercitrin, rutin, taxifolin, myricetin, myrictrin), caffeic acid or esters thereof, terpenoid bitter substances (in particular limonin, nomilin, lupolones and humolones), metal salts (potassium chloride, sodium sulfate, magnesium salts, iron salts, aluminium salts, zinc salts), pharmaceutical active ingredients (e.g. fluoroquinolone antibiotics, paracetamol, aspirin, β-lactam antibiotics, ambroxol, propylthiouracil [PROP], guaifenesin), amino acids (e.g. leucine, isoleucine, valine, tryptophan, proline, histidine, tyrosine, lysine or phenylalanine), peptides (in particular peptides having an amino acid from the group leucine, isoleucine, valine, tryptophan, proline or phenylalanine at the N or C terminus).

Especially preferred bitter substances that are to be masked are selected from the group consisting of caffeine, theobromine, quinine, salicin, arbutin, neohesperidin, eriocitrin, neoeriocitrin, narirutin, hesperidin, naringin, phloridzin, catechin, epicatechin, epigallocatechin gallate (EGCG), gallocatechin, gallocatechin-3-gallate, procyanidin B2, procyanidin B5, procyanidin C1, thearubigenin, rutin, taxifolin, myricetin, myrictrin, caffeic acid or esters thereof, limonin and nomilin, amino acids (e.g. leucine, isoleucine, valine, tryptophan, proline, histidine, tyrosine, lysine or phenylalanine), peptides having an amino acid from the group leucine, isoleucine, valine, tryptophan, proline or phenylalanine at the N or C terminus, potassium chloride, paracetamol, aspirin and β-lactam antibiotics.

Substances that have a bitter, astringent, doughy, chalky, dusty, dry, floury, rancid and/or metallic secondary taste and/or aftertaste can be flavourings and/or taste-imparting substances having a not unpleasant primary taste (for example sweet, salty, spicy, sour) and/or odour and can belong, for example, to the group of the sweeteners, sugar substitutes or flavourings. Examples which may be mentioned include: aspartame, neotam, superaspartame, alitam, saccharin, sucralose, tagatose, monellin, monatin, steviosides, rubusoside, stevioside, rebaudioside A, rebaudioside C, thaumatin, miraculin, glycyrrhizine (glycyrrhizinic acid), glycyrrhetinic acid or derivatives thereof, cyclamate, or the physiologically acceptable salts of the above-mentioned compounds.

Because the bitter intensity of various bitter substances differs significantly, the bitterness of a compound is sometimes indicated in the following in relevant bitterness equivalents (RBE). The known bitter substance caffeine is here used as the reference substance. Determination of the RBE value as a measure of the relative bitterness of a sample is carried out with the aid of a scale of from 1 to 10. A relative bitterness of 1, that is to say an RBE value of 1, corresponds to the bitterness of an amount of caffeine in a dose of 100 mg/kg of sample to be tested. A relative bitterness of 5, that is to say an RBE value of 5, corresponds to the bitterness of an amount of caffeine in a dose of 500 mg/kg of sample to be tested. The sample to be tested can vary considerably in its composition. For example, the sample to be tested can be a preparation for nutrition, oral care, enjoyment, an oral pharmaceutical preparation or a cosmetic preparation, for example a foodstuff, a drink, a chewing gum, a mouthwash, a sweet, a cough syrup or a tablet. The scale used for determining the RBE values corresponds to ISO 4121 [Sensory Analysis—Guidelines for the use of quantitative response scales; A.3 Example 2]. The choice of panellists for determining the RBE values is carried out according to ISO 8586-1 [Sensory analysis—General guidance for the selection, training, and monitoring, of assessors—Part 1: Selected assessors]. The number of panellists corresponds to ISO 8586-I, 4.2.3 [Number of persons to be selected, together with ISO 6658 Sensory analysis—Methodology—General guidance—5.3.5 Scoring (5 or more selected panellists)]. The crucial advantage of the lactic acid menthyl esters to be used according to the invention is that the unpleasant taste of such bitter substances can be compensated for even when they are present in a concentration that corresponds to at least 2 relative bitterness equivalents.

Flavourings

The oral preparations according to the invention can comprise one or more flavourings as an optional component (c).

Surprisingly, it has further been found that the unpleasant taste of an unpleasant-tasting substance as defined above is changed, in particular masked or reduced, particularly well by the lactic acid menthyl esters to be used according to the invention when they are combined with one or more flavourings, preferably flavourings that impart a taste impression that is milky/creamy and gives a sensation of fullness in the mouth and/or that impart a sweet/caramel-like taste impression. Such combinations are accordingly to be regarded as being further mixtures according to the invention. Accordingly, an aspect of the present invention relates to the use of the lactic acid menthyl esters in admixture with one or more flavourings that impart a taste impression that is milky/creamy and gives a sensation of fullness in the mouth and/or that impart a sweet/caramel-like taste impression.

Accordingly, preference is given here too to uses according to the invention in a pharmaceutical preparation or a preparation that serves the purpose of nutrition (in particular foodstuffs based on green or black tea, products based on catechin- and/or tannin-rich, astringent-tasting plant parts (e.g. fruits of particular Rosaceae species, particular apple species, grapes, wine, grape seed extracts, rhubarb, amla, cocoa, maté), products based on soya, and low-fat dairy products, in particular yogurts), of oral care or of enjoyment.

In the case of the uses according to the invention of a mixture comprising one or more flavourings, a total amount of the lactic acid menthyl ester(s) to be used according to the invention that is not sufficient to increase salivation is particularly suitable.

It is particularly surprising that the flavourings preferably used in the uses according to the invention have the positive property of synergistically enhancing the action of the lactic acid menthyl esters in changing, in particular masking or reducing, the unpleasant taste impression. Accordingly, a further aspect of the present invention consists in a use as defined above, wherein the amount of the flavouring(s) that is used synergistically enhances the action of the lactic acid menthyl ester(s) in changing, in particular masking or reducing, the unpleasant taste impression of an unpleasant-tasting substance or substance mixture.

Such a synergistic enhancement occurs in particular when the weight ratio of the amount of lactic acid menthyl esters that is to be used according to the invention and flavourings is in the range of from approximately 1:2 to approximately 1:200, preferably in the range of from approximately 1:3 to approximately 1:100, particularly preferably in the range of from approximately 1:5 to approximately 1:70. Corresponding mixtures are preferred.

In the tests that have been carried out it has been found, moreover, that, in the uses according to the invention of mixtures comprising, as defined above, one or more flavourings, the one or more flavourings are preferably selected from the group consisting of alcohols, aldehydes, ketones, organic acids, esters, lactones, sulfur components, acetals, phenols, furans, pyrans and pyrazines.

Typical examples include: acetophenone, allyl capronate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl capronate, butylidene phthalide, carvone, camphene, caryophyllene, cineol, cinnamyl acetate, citral, citronellol, citronellal, citronellyl acetate, cyclohexyl acetate, cymol, damascone, decalactone, dihydrocoumarin, dimethyl anthranilate, dimethyl anthranilate, dodecalactone, ethoxyethyl acetate, ethylbutyric acid, ethyl butyrate, ethyl caprinate, ethyl capronate, ethyl crotonate, ethylfuraneol, ethylguaiacol, ethyl isobutyrate, ethyl isovalerate, ethyl lactate, ethyl-methyl butyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl capronate, trans-2-hexenyl capronate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamyl isovalerate, isobutyl butyrate, isobutyraldehyde, isoeugenol methyl ether, isopropylmethylthiazole, lauric acid, levulinic acid, linalool, linalool oxide, linalyl acetate, menthol, menthofuran, methyl anthranilate, methylbutanol, methylbutyric acid, 2-methylbutyl acetate, methyl capronate, methyl cinnamate, 5-methylfurfural, 3,2,2-methyl-cyclopentenolone, 6,5,2-methylheptenone, methyl dihydrojasmonate, methyl jasmonate, methyl 2-methylbutyrate, 2-methyl-2-pentenoic acid, methyl thiobutyrate, 3,1-methylthiohexanol, 3-methylthiohexyl acetate, nerol, neryl acetate, trans,trans-2,4-nonadienal, 2,4-nonadienol, 2,6-nonadienol, 2,4-nonadienol, nooctanone, delta-octalactone, gamma octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegon, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3(2H)-furanone and derivatives thereof (preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (preferably ethylmaltol), coumarin and coumarin derivatives, gamma-lactones (preferably gamma-undecalactone, gamma-nonalactone, gamma-decalactone), delta-lactones (preferably 4-methyldeltadecalactone, massoilactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, acetic acid isoamyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl 3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl)disulfide, furfurylmercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamyl alcohol, methyl salicylate, isopulegol, and also stereoisomers, enantiomers, position isomers, diastereoisomers, cis/trans isomers and epimers (not mentioned explicitly here) of those substances.

Particular preference is given to the following flavourings, because they impart a taste impression that is milky/creamy and gives a sensation of fullness in the mouth and/or a sweet/caramel-like taste impression: diacetyl, acetoin, benzaldehyde, furaneol, heliotropin, vanillin, ethylvanillin, ethylvanillin isobutyrate (=3-ethoxy-4-isobutyryloxybenzaldehyde), Furaneol® (2,5-dimethyl-4-hydroxy-3(2H)-furanone) and derivatives thereof (preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (preferably ethylmaltol), coumarin and coumarin derivatives, gamma-lactones (preferably gamma-undecalactone, gamma-nonalactone, gamma-decalactone), delta-lactones (preferably 4-methyldeltadecalactone, massoilactone, deltadecalactone, tuberolactone), methyl sorbate, divanillin, 4-hydroxy-2 (or 5)-ethyl-5(or 2)-methyl-3(2H)furanone, 2-hydroxy-3-methyl-2-cyclopentenone, 3-hydroxy-4,5-dimethyl-2(5H)-furanone, acetic acid isoamyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl 3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde.

Ready-for-Use Products

Oral preparations provided by the present invention are understood in the following as being not only products that serve the purpose of human nutrition but also agents that come into contact with the oral mucosa. Accordingly, that description includes on the one hand foodstuffs and on the other hand oral and tooth cleaning and care agents as well as orally administered pharmaceutical agents.

The oral preparation is preferably baked goods, for example bread, dry biscuits, cakes, other pastries, confectionery (for example chocolates, chocolate bar products, other products in bar form, fruit gums, hard and soft caramels, chewing gum), alcoholic or non-alcoholic drinks (for example coffee, tea, iced tea, (green, black) tea drinks enriched with (green, black) tea extracts, rooibos tea, wine, wine-containing drinks, beer, beer-containing drinks, liqueurs, schnapps, brandies, (carbonated) fruit-containing soft drinks, (carbonated) isotonic drinks, (carbonated) refreshment drinks, nectars, spritzers, fruit and vegetable juices, fruit or vegetable juice preparations, instant drinks (for example instant cocoa drinks, instant tea drinks, instant coffee drinks, instant fruit drinks), meat products (for example ham, fresh sausage or raw sausage preparations, spiced or marinated fish or salt meat products), eggs or egg products (dried egg, egg white, egg yolk), cereal products (for example breakfast cereals, muesli bars, precooked ready-to-eat rice products), dairy products (for example milk drinks, butter-milk drinks, milk ice, yogurt, kefir, cream cheese, soft cheese, hard cheese, dried milk powder, whey, whey drinks, butter, buttermilk, partially or fully hydrolysed milk-protein-containing products), products made from soy protein or other soybean fractions (for example soy milk and products produced therefrom, fruit drinks with soy protein, soy-lecithin-containing preparations, fermented products such as tofu or tempeh or products produced therefrom), products made from other vegetable protein sources, for example oat protein drinks, fruit preparations (for example jams, fruit ice, fruit sauces, fruit fillings), vegetable preparations (for example ketchup, sauces, dried vegetables, frozen vegetables, precooked vegetables, boiled-down vegetables), snack articles (for example baked or fried potato crisps or potato dough products, maize- or peanut-based extrudates), products based on fats and oils or emulsions thereof (for example mayonnaise, remoulade, dressings), other ready meals and soups (for example dried soups, instant soups, precooked soups), spices, spice mixtures and in particular seasonings used, for example, in the snacks sector. Alternatively, toothpastes, mouthwashes, cold remedies or active ingredient capsules come into consideration.

The orally consumable products within the meaning of the invention can also be used as semi-finished products for the production of further orally consumable products. The orally consumable sweet-tasting products within the meaning of the invention can also be present as food supplements in the form of capsules, tablets (uncoated and coated tablets, for example enteric coatings), dragées, granules, pellets, solid mixtures, dispersions in liquid phases, in the form of emulsions, in the form of powders, in the form of solutions, in the form of pastes, or in the form of other preparations which can be swallowed or chewed.

The total amount of components (a) and (b) that is used in the oral preparations can be from approximately 0.001 to approximately 1 wt. % and preferably approximately from 0.01 to 0.5 wt. %, based on the ready-for-use end products. In particular, the amount of lactic acid menthyl esters, based on the semi-finished products or the ready-for-use end products, can be in the range of from 0.05 mg/kg (corresponding to 50 ppb) to 1 g/kg, in particular from 0.1 mg/kg (corresponding to 0.1 ppm) to 900 mg/kg, especially in the range of from 0.5 to 750 mg/kg (corresponding to from 0.5 to 900 ppb), preferably in the range of from 1 to 500 mg/kg, more preferably in the range of from 3 to 300 mg/kg, particularly preferably in the range of from 5 to 200 mg/kg, most preferably in the range of from 10 to 100 mg/kg.

A. Active Ingredients for Masking Unpleasant Taste Impressions

Furthermore, the oral preparations can also comprise further substances that likewise serve to mask bitter and/or astringent taste impressions. These further taste-correcting agents are selected, for example, from the following list: nucleotides (e.g. adenosine 5'-monophosphate, cytidine 5'-monophosphate) or physiologically acceptable salts thereof, lactisols, sodium salts (e.g. sodium chloride, sodium lactate, sodium citrate, sodium acetate, sodium gluconate), hydroxyflavanones, preferably eriodictyol, sterubin (eriodictyol 7-methyl ether), homoeriodictyol, and sodium, potassium, calcium, magnesium or zinc salts thereof (in particular those as described in EP 1258200 A2, which, in respect of the corresponding compounds disclosed therein, forms part of this application by way of reference), hydroxybenzoic acid amides, preferably 2,4-dihydroxybenzoic acid vanillyl amide, 2,4-dihydroxybenzoic acid N-(4-hydroxy-3-methoxybenzyl)amide, 2,4,6-trihydroxybenzoic acid N-(4-hydroxy-3-methoxybenzyl)amide, 2-hydroxybenzoic acid N-4-(hydroxy-3-methoxy-benzyl)amide, 4-hydroxybenzoic acid N-(4-hydroxy-3-methoxybenzyl)amide, 2,4-dihydroxybenzoic acid N-(4-hydroxy-3-methoxy-benzyl)amide monosodium salt, 2,4-dihydroxybenzoic acid N-2-(4-hydroxy-3-methoxy-phenyl)-ethylamide, 2,4-dihydroxybenzoic acid N-(4-hydroxy-3-ethoxybenzyl)amide, 2,4-dihydroxybenzoic acid N-(3,4-dihydroxy-benzyl)amide and 2-hydroxy-5-methoxy-N-[2-(4-hydroxy-3-methoxyphenyl)ethyl]amide; 4-hydroxybenzoic acid vanillylamides (in particular those as described in WO 2006/024587, which, in respect of the corresponding compounds disclosed therein, forms part of this application by way of reference); hydroxydeoxybenzoins, preferably 2-(4-hydroxy-3-methoxyphenyl)-1-(2,4,6-trihydroxy-phenyl)ethanone, 1-(2,4-dihydroxyphenyl)-2-(4-hydroxy-3-methoxyphenyl)-ethanone and 1-(2-hydroxy-4-methoxyphenyl)-2-(4-hydroxy-3-methoxyphenyl)ethanone) (in particular those as described in WO 2006/106023), hydroxyphenylalkanediones, such as, for example, [2]-gingerdione, [3]-gingerdione, [4]-gingerdione, dehydro-[2]-gingerdione, dehydro-[3]-gingerdione, dehydro-[4]-gingerdione) (in particular those as described in WO 2007/003527), diacetyltrimers (in particular those as described in WO 2006/058893); gamma-aminobutyric acids (in particular those as described in WO 2005/096841); divanillins (in particular those as described in WO 2004/078302) and 4-hydroxydihydrochalcones (preferably as described in US 2008/0227867 A1), in particular phloretin and davidigenin, amino acids or mixutres of whey proteins with lecithins, hesperetin as disclosed in WO 2007/014879, 4-hydroxydihydrochalcones as disclosed in WO 2007/107596, or propenylphenylglycosides (chavicol glycosides) as described in EP 1955601 A1, or extracts from *Rubus suavissimus*, extracts from *Hydrangea macrophylla* as described in EP 2298084 A1, pellitorine and derived flavour compositions as described in EP 2008530 A1, umami compounds as described in WO 2008/046895 A1 and EP 1989944 A1, umami compounds as described in EP 2064959 A1 or EP 2135516 A1, vanillyl lignanes, enterodiol, and N-decadienoyl-amino acids and mixtures thereof.

B. Sweeteners

The oral preparations can in particular also comprise sweeteners, which are selected, for example, from the following groups:

carbohydrates, or sugars, selected from the subgroup consisting of sucrose, D-fructose, D-glucose and highly enriched fructose syrups from corn starch (high fructose corn syrup);

sweeteners selected from the subgroup consisting of stevioside, rebaudioside A and rubusoside, it also being possible to use extracts or enriched fractions of those extracts, for example Stevia extracts and *Rubus suavissimus* extracts;

naturally occurring sweeteners selected from the subgroup consisting of miraculin, curculin, monellin, mabinlin, thaumatin, curculin, brazzein, pentadin, D-phenylalanine, D-tryptophan and mixtures thereof;

naturally occurring sweeteners selected from the subgroup consisting of stevioside, steviolbioside, rebaudioside A, further steviol glycosides such as rebaudioside B, rebaudioside C, rebaudioside D, rebaudioside E, rebaudioside F, rebaudioside G, rebaudioside H, dulcoside and/or rubusoside, oslandin, polypodoside A, strogin 1, strogin 2, strogin 4, selligueain A, dihydroquercetin 3-acetate, perillartin, telosmoside $A_{15}$, periandrin I-V, phyllodulcin, pterocaryosides, cyclocaryosides, mukuroziosides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanin, chlorogenic acid, Albizia saponin, telosmosides, gaudichaudioside, mogrosides, hernandulcin, glycyrrhetinic acid, balansin A, balansin B and mixtures thereof;

sweetness-enhancing flavourings and/or taste-imparting substances including the physiologically acceptable salts thereof, selected from the group consisting of hesperetin, phloretin, phyllodulcin or extracts containing phyllodulcin, balansin A and/or balansin B or extracts from *Mycetia balansae*, containing balansin A and/or Balansin B, 3′,7-dihydroxy-4′-methoxyflavone, (S)-3′,7-dihydroxy-4′-methoxy-flavone, 1-(2,4-dihydroxy-phenyl)-3-(3-hydroxy-4-methoxy-phenyl)-propan-1-one, and mixtures thereof.

C. Taste-Enhancing Agents and Flavourings

The preparations can further comprise additional flavourings for bringing about or enhancing a salty, optionally slightly acidic and/or umami taste impression. Preference is given to salty-tasting compounds and salt-enhancing compounds. Preferred compounds are disclosed in WO 2007/045566 A1. Preference is given also to umami compounds as described in WO 2008/046895 A1 and EP 1989944 A1.

Preferred flavourings are those which cause a sweet taste impression, the further flavouring(s) that cause a sweet taste impression preferably being selected from the group consisting of:

vanillin, ethylvanillin, ethylvanillin isobutyrate (=3-ethoxy-4-isobutyryloxybenzaldehyde), Furaneol® (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and derivatives (e.g. ethylmaltol), coumarin and derivatives, gamma-lactones (e.g. gamma-undecalactone, gamma-nonalactone), delta-lactones (e.g. 4-methyldeltalactone, massoilactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones (e.g. acetic acid n-butyl ester, acetic acid isoamyl ester, propionic acid ethyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl 3-methyl-3-phenylglycidate, ethyl 2-trans-4-cis-decadienoate), 4-(p-hydroxyphenyl)-2-butanone, 1,1-dimethoxy-2,2,5-trimethyl-4-hexane, 2,6-dimethyl-5-hepten-1-al, 4-hydroxycinnannic acid, 4-methoxy-3-hydroxycinnamic acid, 3-methoxy-4-hydroxycinnamic acid, 2-hydroxycinnamic acid, 2,4-dihydroxybenzoic acid, 3-hydroxybenzoic acid, 3,4-dihydroxybenzoic acid, vanillic acid, homovanillinic acid, vanillomandelic acid and phenylacetaldehyde.

D. Further Auxiliary Substances and Additives

Examples of conventional base materials, auxiliary substances and additives are water, mixtures of fresh or processed, vegetable or animal base or raw materials (for example raw, roasted, dried, fermented, smoked and/or boiled meat, bones, cartilage, fish, vegetables, fruits, herbs, nuts, vegetable or fruit juices or pastes or mixtures thereof), digestible or non-digestible carbohydrates (for example dextrins, amylose, amylopectin, inulin, xylanes, cellulose), natural or hardened fats (for example tallow, lard, palm fat, coconut fat, hardened vegetable fat), oils (for example sunflower oil, groundnut oil, cornseed oil, olive oil, fish oil, soy oil, sesame oil), fatty acids or salts thereof (for example potassium stearate), proteinogenic or non-proteinogenic amino acids and related compounds (for example taurine), peptides, natural or processed proteins (for example gelatin), enzymes (for example peptidases), nucleic acids, nucleotides, taste-correcting agents for unpleasant taste impressions other than the above-described taste-correcting agents, taste-correcting agents for further, generally not unpleasant taste impressions, taste-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols), stabilisers (for example carageenan, alginate), preservatives (for example benzoic acid, sorbic acid), antioxidants (for example tocopherol, ascorbic acid), chelators (for example citric acid), organic or inorganic acidifying agents (for example malic acid, acetic acid, citric acid, tartaric acid, phosphoric acid), additional bitter substances (for example quinine, caffeine, limonin, amarogentin, humolones, lupolones, catechins, tannins), mineral salts (for example sodium chloride, potassium chloride, magnesium chloride, sodium phosphates), substances that prevent enzymatic browning (for example sulfite, ascorbic acid), ethereal oils, plant extracts, natural or synthetic colourants or colouring pigments (for example carotinoids, flavonoids, anthocyans, chlorophyll and derivatives thereof), spices, synthetic, natural or nature-identical flavourings or fragrances as well as odour-correcting agents.

E. Drinks

As oral preparations which can comprise the lactic acid menthyl esters to be used according to the invention there may be mentioned in particular drinks, which can also be carbonated. Preferred drinks according to the invention are optionally carbonated, acid- and fruit-containing iced teas, optionally enriched with catechins or plant extracts, soft drinks (for example orange, lime or lemon type), carbonated isotonic drinks (for example orange, lime or lemon type), carbonated, acidic refreshment drinks (for example cola, lemon, orange, lime, cherry, apple, vanilla type or mixtures thereof), carbonated spritzers, carbonated fruit and vegetable juices, carbonated fruit or vegetable juice preparations. Within the meaning of the invention, carbonated means that the drink contains carbon dioxide that has been introduced naturally (e.g. from fermentation processes as in beer production or by water from carbon-dioxide-containing mineral sources) or that carbon dioxide has been added thereto during the production and/or bottling process.

These can comprise as preferred auxiliary substances or carriers maltodextrin, starch, natural or synthetic polysaccharides and/or plant gums such as modified starches or gum arabic, solvents approved for flavour mixtures, such as, for example, ethanol, 1,2-propylene glycol, water, glycerol, triacetin, vegetable oil triglycerides, colouring agents, for example approved food colourants, colouring plant extracts, stabilisers, preservatives, antioxidants and viscosity-influencing substances.

Particularly preferred orally consumable sweet-tasting products within the meaning of the invention are alcoholic drinks such as beer mix drinks, wine mix drinks or other mixed drinks containing not more than 5 vol. % alcohol, and/or non-alcoholic drinks such as tea, iced tea (sweetened, for example also with herb flavours or fruit flavours of the lime, orange type), (carbonated) fruit-containing soft drinks (for example orange, lime or lemon type), (carbonated) isotonic drinks (for example orange, lime or lemon type), (carbonated) refreshment drinks (for example cola, lemon, orange, lime, cherry, apple, vanilla type or mixtures thereof), nectars, spritzers, milk drinks, buttermilk drinks, yogurt, kefir, whey drinks, soy milk and products produced therefrom, fruit drinks with soy protein, oat protein drinks, and instant drinks (for example instant cocoa drinks, instant tea drinks, instant coffee drinks, instant fruit drinks), so-called flavoured waters ("near water" drinks), which must be sweetened.

"Near water" drinks within the meaning of this text are (carbonated) drinks based on (mineral) water, which in most cases are clear, are only slightly coloured, are often only slightly sweetened (less than 5% sucrose or sweeteners having a sweetening power of less than 5% sucrose), in most cases are not acidified at all or are acidified only slightly and have a pH range of approximately from 4 to 8, in most cases are only flavoured and can also be provided with minerals, vitamins and/or plant extracts. Unlike most other drinks (e.g. soft drinks, fruit juice drinks, [iced] tea drinks, etc.), the "water" nature of the drink is still at the forefront.

Preference is given to drinks that have a pH value of less than 7, particularly preferably less than 5, most particularly preferably less than 4.

F. Oral and Tooth Care Agents

Orally consumable sweet-tasting products according to the invention can also be used for oral and tooth cleaning and care. Examples thereof are toothpastes, tooth gels, tooth powders, mouthwashes and the like. Toothpastes or tooth creams are generally understood as being gel-like or pasty preparations comprising water, thickeners, humectants, abrasive or cleaning agents, surfactants, sweeteners, flavourings, deodorising active ingredients and active ingredients against oral and tooth diseases. All conventional cleaning agents, such as, for example, chalk, dicalcium phosphate, insoluble sodium metaphosphate, aluminium silicates, calcium pyrophosphate, finely divided synthetic resins, silicas, aluminium oxide and aluminium oxide trihydrate, can be used in the toothpastes according to the invention.

Preferred suitable cleaning agents for the toothpastes according to the invention are especially finely divided xerogel silicas, hydrogel silicas, precipitated silicas, aluminium oxide trihydrate and finely divided alpha-aluminium oxide or mixtures of those cleaning agents in amounts of from 15 to 40 wt. % of the toothpastes.

Suitable humectants are predominantly low molecular weight polyethylene glycols, glycerol, sorbitol or mixtures of those products in amounts of up to 50 wt. %. Among the known thickeners, the thickening, finely divided gel silicas and hydrocolloids, such as, for example, carboxymethyl cellulose, hydroxyethyl cellulose, hydroxypropylguar, hydroxyethyl starch, polyvinylpyrrolidone, high molecular weight polyethylene glycol, plant gums such as tragacanth, agar-agar, carrageen moss, gum arabic, xanthan gum and carboxyvinyl polymers (e.g. Carbopol® types) are suitable.

The oral and tooth care agents can additionally comprise in particular surface-active substances, preferably anionic and non-ionic high-foam surfactants, such as the substances already mentioned above, but in particular alkyl ether sulfate salts, alkyl polyglucosides and mixtures thereof. Further conventional toothpaste additives are:

preservatives and antimicrobial substances, such as, for example, p-hydroxybenzoic acid methyl, ethyl or propyl ester, sodium sorbate, sodium benzoate, bromochlorophene, phenylsalicylic acid ester, thymol and the like;

anti-tooth-staining active ingredients, for example organophosphates such as 1-hydroxyethane-1,1-diphosphonic acid, 1-phosphonopropane-1,2,3-tricarboxylic acid and others, which are known, for example, from U.S. Pat. No. 3,488,419, DE 2224430 A1 and DE 2343196 A1;

other caries-inhibiting substances, such as, for example, sodium fluoride, sodium monofluorophosphate, tin fluoride;

sweeteners, such as, for example, saccharin sodium, sodium cyclamate, sucrose, lactose, maltose, fructose or Aspartame®, (L-aspartyl-L-phenylalanine methyl ester), stevia extracts or the sweetening constituents thereof, in particular rebaudiosides;

taste-modulating substances (for example inositol phosphate, nucleotides such as guanosine monophosphate, adenosine monophosphate or other substances such as sodium glutamate or 2-phenoxypropionic acid);

cooling active ingredients such as, for example, menthol, menthol derivatives (for example L-menthol, L-menthyl lactate, L-menthyl alkyl carbonates, menthone ketals, menthane carboxylic acid amides), 2,2,2-trialkylacetic acid amides (for example 2,2-diisopropylpropionic acid methyl amide), icilin derivatives;

additional flavours such as, for example, eucalyptus oil, aniseed oil, fennel oil, caraway oil, methyl acetate, cinnamaldehyde, anethole, vanillin, thymol and mixtures of these and other natural and synthetic flavours;

pigments such as, for example, titanium dioxide;

colourants;

buffer substances such as, for example, primary, secondary or tertiary alkali phosphates or citric acid/sodium citrate;

wound-healing and anti-inflammatory substances such as, for example, allantoin, urea, azulene, camomile active ingredients and acetylsalicylic acid derivatives.

A preferred embodiment of the cosmetic preparations are toothpastes in the form of an aqueous, pasty dispersion comprising polishing agents, humectants, viscosity regulators and optionally further conventional components, as well as the mixture of menthofuran and menthol compounds in amounts of from 0.5 to 2 wt. %.

In mouthwashes, a combination with aqueous-alcoholic solutions of different concentrations of ethereal oils, emulsifiers, astringent and stimulating drug extracts, tartar-inhibiting, antibacterial additives and taste-correcting agents is readily possible. A further preferred embodiment of the invention is a mouthwash in the form of an aqueous or aqueous-alcoholic solution comprising a mixture of menthofuran and menthol compounds in amounts of from 0.5 to 2 wt. %. In mouthwashes that are diluted prior to use, adequate effects can be achieved with higher concentrations, corresponding to the intended dilution ratio.

In order to improve the flow behaviour, hydrotropic agents, such as, for example, ethanol, isopropyl alcohol or polyols, can be used; these substances largely correspond to the carriers described at the beginning. Polyols that come into consideration here preferably have from 2 to 15 carbon atoms and at least two hydroxyl groups. The polyols can also contain further functional groups, in particular amino groups, or can be modified with nitrogen. Typical examples are glycerol;

alkylene glycols, such as, for example, ethylene glycol, diethylene glycol, propylene glycol, butylene glycol, hexylene glycol and polyethylene glycols having an average molecular weight of from 100 to 1000 daltons;

technical oligoglycerol mixtures having a degree of self-condensation of from 1.5 to 10, such as, for example, technical diglycerol mixtures having a diglycerol content of from 40 to 50 wt. %;

methylol compounds, such as, in particular, trimethylolethane, trimethylolpropane, trimethylolbutane, pentaerythritol and dipentaerythritol;

lower alkyl glucosides, in particular those having from 1 to 8 carbon atoms in the alkyl moiety, such as, for example, methyl and butyl glucoside;

sugar alcohols having from 5 to 12 carbon atoms, such as, for example, sorbitol or mannitol;

sugars having from 5 to 12 carbon atoms, such as, for example, glucose or sucrose;

amino sugars, such as, for example, glucamine;

dialcohol amines, such as diethanolamine or 2-amino-1,3-propanediol.

Suitable preservatives are, for example, phenoxyethanol, formaldehyde solution, parabens, pentanediol or sorbic acid as well as the silver complexes known by the name Surfacine® and the further substance classes listed in Annex 6, Parts A and B of the cosmetics regulation.

G. Chewing Gums

The preferred oral preparations can also be chewing gums. These products typically comprise a water-insoluble component and a water-soluble component.

The water-insoluble base, which is also referred to as the "gum base", conventionally comprises natural or synthetic elastomers, resins, fats and oils, plasticisers, fillers, colourants and optionally waxes. The amount of base in the total composition is conventionally from 5 to 95 wt. %, preferably from 10 to 50 wt. % and in particular from 20 to 35 wt. %. In a typical embodiment of the invention, the base is composed of from 20 to 60 wt. % synthetic elastomers, from 0 to 30 wt. % natural elastomers, from 5 to 55 wt. % plasticisers, from 4 to 35 wt. % fillers and, in subordinate amounts, additives such as colourants, antioxidants and the like, with the proviso that they are water-soluble at most in small amounts.

Suitable synthetic elastomers are, for example, polyisobutylenes having average molecular weights (according to GPC) of from 10,000 to 100,000 and preferably from 50,000 to 80,000, isobutylene-isoprene copolymers ("butyl elastomers"), styrene-butadiene copolymers (styrene:butadiene ratio e.g. from 1:3 to 3:1), polyvinyl acetates having average molecular weights (according to GPC) of from 2000 to 90,000 and preferably from 10,000 to 65,000, polyisoprenes, polyethylene, vinyl acetate-vinyl laurate copolymers and mixtures thereof. Examples of suitable natural elastomers are rubbers such as, for example, smoked or liquid latex or guayule as well as natural rubbers such as jelutong, lechi caspi, perillo, sorva, massaranduba balata, massaranduba chocolate, nispero, rosindinba, chicle, gutta hang kang and mixtures thereof. The choice of synthetic and natural elastomers and the mixing ratios thereof is determined substantially by whether bubbles are to be produced with the chewing gums (bubble gums) or not. Elastomer mixtures comprising jelutong, chicle, sorva and massaranduba are preferably used.

In most cases, the elastomers are found to be too hard or to have insufficient deformability on processing, so that it has been found to be advantageous to use concomitantly particular plasticisers, which of course must also meet in particular all the requirements for approval as food additives. In this respect there come into consideration especially esters of resin acids, for example esters of lower aliphatic alcohols or polyols with wholly or partially hardened, monomeric or oligomeric resin acids. The methyl, glycerol or pentaerythritol esters in particular, and mixtures thereof, are used for this purpose. Alternatively, there come into consideration also terpene resins, which can be derived from alpha-pinene, beta-pinene, delta-limonene or mixtures thereof.

There come into consideration as fillers or texturising agents magnesium or calcium carbonate, ground pumice, silicates, especially magnesium or aluminium silicates, clays, aluminium oxides, talcum, titanium dioxide, mono-, di- and tri-calcium phosphate as well as cellulose polymers.

Suitable emulsifiers are tallow, hardened tallow, hardened or partially hardened vegetable oils, cocoa butter, partial glycerides, lecithin, triacetin, and saturated or unsaturated fatty acids having from 6 to 22 carbon atoms and preferably from 12 to 18 carbon atoms, and mixtures thereof.

Suitable colourants and whitening agents are, for example, the FD and C types approved for the colouring of foodstuffs, plant and fruit extracts and also titanium dioxide.

The base compositions can contain waxes or be wax-free; examples of wax-free compositions are to be found inter alia in patent specification U.S. Pat. No. 5,286,500, to the content of which reference is hereby expressly made.

In addition to the water-insoluble gum base, chewing gum preparations generally comprise a water-soluble component, which is formed, for example, by softeners, sweeteners, fillers, taste-imparting substances, taste enhancers, emulsifiers, colourants, acidifying agents, antioxidants and the like, with the proviso that the constituents have at least sufficient water solubility. Depending on the water solubility of the particular representatives, individual constituents can accordingly belong to both the water-insoluble phase and the water-soluble phase. It is, however, also possible to use combinations, for example, of a water-soluble and a water-insoluble emulsifier, in which case the individual representatives are in different phases. The water-insoluble component conventionally accounts for from 5 to 95 wt. % and preferably from 20 to 80 wt. % of the preparation.

Water-soluble softeners or plasticising agents are added to the chewing gum preparations in order to improve the chewability and chewing sensation and are present in the mixtures typically in amounts of from 0.5 to 15 wt. %. Typical examples are glycerol, lecithin as well as aqueous solutions of sorbitol, hardened starch hydrolysates or corn syrup.

Suitable sweeteners are both sugar-containing and sugar-free compounds, which are used in amounts of from 5 to 95 wt. %, preferably from 20 to 80 wt. % and in particular from 30 to 60 wt. %, based on the chewing gum composition. Typical saccharide sweeteners are sucrose, dextrose, maltose, dextrin, dried invert sugar, fructose, levulose, galactose, corn syrup and mixtures thereof. Suitable sugar substitutes are sorbitol, mannitol, xylitol, hardened starch hydrolysates, maltitol and mixtures thereof. There also come into consideration as additives so-called HIAS (high intensity artificial sweeteners), such as, for example, sucralose, aspartame, acesulfame salts, alitam, saccharin and saccharin salts, cyclamic acid and salts thereof, glycyrrhizins, dihydrochalcones, thaumatin, monellin and the like, alone or in blends. The hydrophobic HIAS which are the subject of international patent application WO 2002 091849 A1 (Wrigleys), as well as stevia extracts and the active constituents thereof, in particular ribeaudioside A, are also particularly effective. The amount of these substances that is used depends primarily on their efficacy and is typically in the range of from 0.02 to 8 wt. %.

In particular for the production of low-calorie chewing gums, fillers such as, for example, polydextrose, raftilose, rafitiline, fructooligosaccharides (NutraFlora), palatinose oligosaccharides, guar gum hydrolysates (Sun Fiber) and dextrins are suitable.

The choice of further taste-imparting substances is virtually unlimited and is not important for the nature of the invention. The total amount of all taste-imparting substances is conventionally from 0.1 to 15 wt. % and preferably from 0.2 to 5 wt. %, based on the chewing gum composition. Suitable further taste-imparting substances are, for example, essential oils, synthetic flavours and the like, such as, for example, aniseed oil, star anise oil, caraway oil, eucalyptus oil, fennel oil, lemon oil, wintergreen oil, clove oil and the like, as are also used, for example, in oral and tooth care agents.

The chewing gums can further comprise auxiliary substances and additives which are suitable, for example, for tooth care, especially for controlling plaque and gingivitis, such as, for example, chlorhexidine, CPC or triclosan. pH regulators (e.g. buffers or urea), active ingredients against caries (e.g. phosphates or fluorides), biogenic active ingredients (antibodies, enzymes, caffeine, plant extracts) can further be present, provided that these substances are approved for foodstuffs and do not interact with one another in an undesirable manner.

H. Pharmaceutical Preparations

If the oral preparations are pharmaceutical agents, they comprise a pharmaceutical active ingredient. Advantageous pharmaceutical active ingredients are, for example, steroidal anti-inflammatory substances of the corticosteroid type, such as, for example, hydrocortisone, hydrocortisone derivatives such as hydrocortisone 17-butyrate, dexamethasone, dexamethasone phosphate, methylprednisolone or cortisone.

Advantageous non-steroidal pharmaceutical active ingredients are, for example, anti-inflammatories such as oxicams such as piroxicam or tenoxicam; salicylates such as Aspirin® (acetylsalicylic acid), disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, flurbiprofen, benoxaprofen, or pyrazoles such as phenylbutazone, oxyphenylbutazone, febrazone or azapropazone.

Particularly preferred pharmaceutical preparations are non-prescription products and OTC (over the counter) preparations, comprising active ingredients such as paracetamol, acetylsalicylic acid or ibuprofen, vitamins (for example vitamin H, B-group vitamins such as vitamin B1, B2, B6, B12, niacin, pantothenic acid, preferably in the form of (effervescent) tablets or capsules), minerals (preferably in the form of (effervescent) tablets or capsules) such as iron salts, zinc salts, selenium salts, products comprising active ingredients or extracts from ribwort (for example in cough syrup) or St. John's wort.

I. Capsules

The oral preparations can also be incorporated into emulsions, into liposomes, for example starting from phosphatidylcholine, into microspheres, into nanospheres and in particular also into capsules, granules or extrudates of a matrix suitable for foodstuffs and luxury foods, for example of starch, starch derivatives, cellulose or cellulose derivatives (for example hydroxypropyl cellulose).

In a further preferred embodiment, the flavour mixtures according to the invention are complexed with one or more suitable complexing agents, for example with cycloglycans, for example cyclofructans, cyclodextrins or cyclodextrin derivatives, preferably α-, γ- and β-cyclodextrin, and used in that complexed form as a ready-for-use end product, that is to say as an oral preparation. Particular preference is given to an orally consumable sweet-tasting product according to the invention in which the matrix is so chosen that the flavour mixture according to the invention is released from the matrix in a delayed manner so that a long-lasting action is obtained.

In addition to conventional macrocapsules based on gelatin, there come into consideration especially also so-called micro- or nano-capsules. These are understood by the person skilled in the art as being spherical aggregates with a diameter in the range of from approximately 0.0001 to approximately 5 mm and preferably from 0.005 to 0.5 mm, which comprise at least one solid or liquid core that is enclosed in at least one continuous shell. More precisely, they are finely dispersed liquid or solid phases encased in film-forming polymers, in the production of which the polymers, after emulsification and coacervation or interfacial polymerisation, precipitate on the material to be encased. According to another process, molten waxes are taken up in a matrix (microsponge), which molten waxes, as microparticles, can additionally be encased in film-forming polymers. According to a third process, particles are coated alternately with polyelectrolytes of different charges (layer-by-layer process). The microscopically small capsules can be dried like powders. In addition to single-core microcapsules there are also known multicore aggregates, also called microspheres, which comprise two or more cores distributed in the continuous shell material. Single- or multi-core microcapsules can additionally be enclosed in an additional second, third, etc. shell. The shell can consist of natural, semi-synthetic or synthetic materials. Natural shell materials are, for example, gum arabic, agar-agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolysates, sucrose and waxes. Semi-synthetic shell materials are inter alia chemically modified celluloses, in particular cellulose esters and ethers, for example cellulose acetate, ethyl cellulose, hydroxypropyl cellulose, hydroxypropylmethyl cellulose and carboxymethyl cellulose, as well as starch derivatives, in particular starch ethers and esters. Synthetic shell materials are, for example, polymers such as polyacrylates, polyamides, polyvinyl alcohol or polyvinylpyrrolidone. Examples of microcapsules of the prior art are the following commercial products (the shell material is given in brackets in each case): Hallcrest Microcapsules (gelatin, gum arabic), Coletica Thalaspheres (maritime collagen), Lipotec millicapsules (alginic acid, agar-agar), Induchem Unispheres (lactose, microcrystalline cellulose, hydroxypropylmethyl cellulose); Unicerin C30 (lactose, microcrystalline cellulose, hydroxypropylmethyl cellulose), Kobo Glycospheres (modified starch, fatty acid esters, phospholipids), Softspheres (modified agar-agar) and Kuhs Probiol Nanospheres (phospholipids) as well as Primaspheres and Primasponges (chitosan, alginates) and Primasys (phospholipids). Coacervates of cationic polymers, in particular of chitosan, with anionic polymers, especially alginates, are of particular interest for the encapsulation of preparations for cosmetic applications. Corresponding processes are described, for example, in publications WO 2001 001926, WO 2001 001927, WO 2001 001928 and WO 2001 001929 (Cognis).

Microcapsules frequently contain the active ingredients dissolved or dispersed in a gel phase. There come into consideration as gel-forming agents preferably those substances which exhibit the property of forming gels in aqueous solution at temperatures above 40° C. Typical examples thereof are heteropolysaccharides and proteins. Suitable thermogelling heteropolysaccharides are preferably agaroses, which can also be present in the form of the agar-agar to be obtained from red algae, together with up to 30 wt. % of non-gel-forming agaropectins. The main constituent of agaroses is linear polysaccharides of D-galactose and 3,6-anhydro-L-galactose, which are linked alternately via β-1,3- and β-1,4-glycosidic linkages. The heteropolysaccharides preferably have a molecular weight in the range of from 110,000 to 160,000 and are both colourless and odourless. Suitable alternatives are pectins, xanthans (also xanthan gum) and mixtures thereof. Preference is further given to those types which, in 1 wt. % aqueous solution, still form gels that do not melt below 80° C. and already solidify again above 40° C. The various gelatin types may be mentioned as examples from the group of the thermogelling proteins.

Suitable cationic polymers are, for example, cationic cellulose derivatives, such as, for example, a quaternised hydroxyethyl cellulose which is obtainable under the name Polymer JR 400® from Amerchol, cationic starch, copolymers of diallylammonium salts and acrylamides, quaternised vinylpyrrolidone/vinylimidazole polymers, such as, for example, Luviquat® (BASF), condensation products of polyglycols and amines, quaternised collagen polypeptides, such as, for example, lauryldimonium hydroxypropyl hydrolyzed collagen (Lamequat®L/Grünau), quaternised wheat polypeptides, polyethyleneimine, cationic silicone polymers, such as, for example, amodimethicone, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides and crosslinked water-soluble polymers thereof, cationic chitin derivatives such as, for example, quaternised chitosan, optionally with microcrystalline distribution, condensation products of dihaloalkyls, such as, for example, dibromobutane, with bisdialkylamines, such as, for example, bis-dimethylamino-1,3-propane, cationic guar gum, such as, for example, Jaguar® CBS, Jaguar® C-17, Jaguar® C-16 from Celanese, quaternised ammonium salt polymers, such as, for example, Mirapol® A-15, Mirapol® AD-1, Mirapol® AZ-1 from Miranol. Chitosan is preferably used as the encapsulating material. Chitosans are biopolymers and belong to the group of the hydrocolloids. From a chemical point of view, they are partially deacetylated chitins of different molecular weights which contain the following—idealised—monomer structural unit:

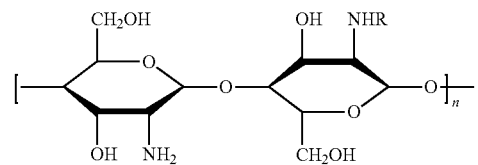

Unlike most hydrocolloids, which are negatively charged in the range of biological pH values, chitosans are cationic biopolymers under those conditions. The positively charged chitosans can interact with the oppositely charged surfaces and are therefore used in cosmetic hair and body care agents as well as in pharmaceutical preparations. Chitosans are produced starting from chitin, preferably the shell residues of crustaceans, which are available in large amounts as inexpensive raw materials. The chitin is conventionally first deprotonated by the addition of bases in a process which was described for the first time by Hackmann et al., demineralised by the addition of mineral acids and finally deacetylated by the addition of strong bases, it being possible for the molecular weights to be distributed over a wide spectrum. Preference is given to the use of those types which have an average molecular weight of from 10,000 to 500,000 or from 800,000 to 1,200,000 daltons and/or a viscosity according to Brookfield (1 wt. % in glycolic acid) below 5000 mPas, a degree of deacetylation in the range of from 80 to 88% and an ash content of less than 0.3 wt. %. For reasons of better water solubility, the chitosans are generally used in the form of their salts, preferably in the form of the glycolates.

The anionic polymers have the function of forming membranes with the cationic polymers. There are suitable for that purpose preferably salts of alginic acid. Alginic acid is a mixture of carboxyl-group-containing polysaccharides with the following idealised monomer structural unit:

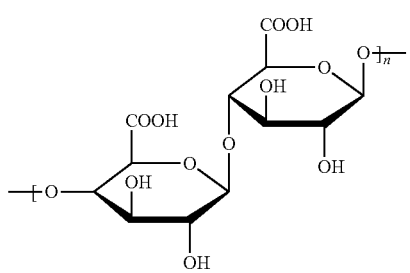

The average molecular weight of alginic acids or alginates is in the range of from 150,000 to 250,000. Salts of alginic acid are to be understood as being both complete and partial neutralisation products thereof, in particular the alkali salts and, of those, preferably sodium alginate ("algin"), as well as the ammonium and alkaline earth salts. Particular preference is given to mixed alginates, such as, for example, sodium/magnesium or sodium/calcium alginates. In an alternative embodiment of the invention, however, anionic chitosan derivatives, such as, for example, carboxylation and especially succinylation products, are also suitable for this purpose. Alternatively, poly(meth)acrylates with average molecular weights in the range of from 5000 to 50,000 daltons as well as the various carboxymethyl celluloses are also suitable. Instead of the anionic polymers, anionic surfactants or low molecular weight inorganic salts, such as, for example, pyrophosphates, can also be used to form the shell membrane.

In order to produce the microcapsules, a from 1 to 10 wt. %, preferably from 2 to 5 wt. %, aqueous solution of the gel-forming agent, preferably of agar-agar, is conventionally prepared and heated under reflux. At boiling, preferably at from 80 to 100° C., there is added a second aqueous solution containing the cation polymer, preferably chitosan, in amounts of from 0.1 to 2 wt. %, preferably from 0.25 to 0.5 wt. %, and the active ingredients in amounts of from 0.1 to 25 wt. % and in particular from 0.25 to 10 wt. %; this mixture is referred to as the matrix. The loading of the microcapsules with active ingredients can therefore likewise be from 0.1 to 25 wt. %, based on the capsule weight. If desired, water-insoluble constituents, for example inorganic pigments, can also be added at this time for viscosity adjustment, such constituents generally being added in the form of aqueous or aqueous/alcoholic dispersions. For emulsifying or dispersing the active ingredients, it can further be useful to add emulsifiers and/or solubilisers to the matrix. After preparation of the matrix of gel-forming agent, cation polymer and active ingredients, the matrix can optionally be very finely dispersed in an oil phase with intensive shear in order to produce particles that are as small as possible in the subsequent encapsulation. It has been found to be particularly advantageous to heat the matrix at temperatures in the range of from 40 to 60° C., while the oil phase is cooled to from 10 to 20° C. In the last, obligatory step, the actual encapsulation takes place, that is to say the formation of the shell membrane by bringing the cation polymer in the matrix into contact with the anionic polymers. To that end it is recommended to treat the matrix, optionally dispersed in the oil phase, at a temperature in the range of from 40 to 100° C., preferably from 50 to 60° C., with an aqueous, approximately from 1 to 50 wt. % and preferably from 10 to 15 wt. % aqueous solution of the anion polymer and—if necessary—remove the oil phase simultaneously or subsequently. The resulting aqueous preparations generally have a microcapsule content in the range of from 1 to 10 wt. %. In some cases it can be advantageous for the solution of the polymers to comprise further ingredients, for example emulsifiers or preservatives. After filtration, microcapsules are obtained which, on average, have a diameter in the range of preferably approximately from 0.01 to 1 mm. It is recommended to screen the capsules in order to ensure that the size distribution is as uniform as possible. Within the context of the production, the microcapsules so obtained can have any desired form, but they are preferably approximately spherical. Alternatively, it is also possible to use the anion polymers to produce the matrix and to carry out the encapsulation with the cation polymers, especially chitosans.

Alternatively, the encapsulation can also be carried out using only cation polymers, use being made of their property of coagulating at pH values above the pKs value.

In a second alternative process, the microcapsules according to the invention are produced by first preparing an O/W emulsion which comprises, in addition to the oil component, water and the active ingredients, an effective amount of emulsifier. In order to produce the matrix, a corresponding amount of an aqueous anion polymer solution is added to this preparation with vigorous stirring. Membrane formation takes place by addition of the chitosan solution. The whole operation preferably takes place in the weakly acidic range at pH=from 3 to 4. If required, the pH is adjusted by the addition of mineral acid. After the membrane formation, the pH value is raised to from 5 to 6, for example by addition of triethanolamine or another base. This leads to an increase in the viscosity, which can be further assisted by the addition of further thickeners, such as, for example, polysaccharides, in particular xanthan gum, guar-guar, agar-agar, alginates and tyloses, carboxymethyl cellulose and hydroxyethyl cellulose, higher molecular weight polyethylene glycol mono- and di-esters of fatty acids, polyacrylates, polyacrylamides and the like. Finally, the microcapsules are separated from the aqueous phase, for example, by decantation, filtration or centrifugation.

In a third alternative process, the formation of the microcapsules takes place around a preferably solid, for example crystalline, core by encasing it layer-wise with oppositely charged polyelectrolytes. Reference may be made in this connection to European patent EP 1064088 B1 (Max-Planck Gesellschaft).

INDUSTRIAL APPLICABILITY

Two further subject-matters of the present invention relate on the one hand to a method of masking unpleasant taste impressions in preparations for oral consumption, in which there is added thereto an effective amount of a lactic acid l-menthyl ester, and on the other hand to the use of said lactic acid l-menthyl esters for masking unpleasant taste impressions in preparations for oral consumption. The amounts used can be in the region of significantly less than 5 mg/kg, preferably less than 2 mg/kg and preferably from approximately 0.005 to approximately 0.1 mg/kg—in each case based on the total preparation.

EXAMPLES

Example 1

Reducing the Astringency Over Time of Epigallocatechin Gallate

In order to evaluate different attributes of a sample simultaneously over a particular period of time, the method of so-called "multiple time-intensity profiling" (mITP) was used. This descriptive method combines the advantages of the "dual-attribute time-intensity" (DATI) method, in which the intensities of two descriptors can be plotted on a two-dimensional plane, and the "time-intensity profiling" (TIP) method, in which more than two descriptors are evaluated in succession over time.

In each mITP test, trained panellists (n=15) are asked to take 2 mouthfuls (each 5 ml) of the sample to be evaluated, to wet the entire oral cavity therewith, and then to spit the sample out again. Measurement begins by marking the intensities of a plurality of descriptors on horizontal linear scales, which are displayed on the computer screen. A linear scale is displayed for each descriptor. A parallel evaluation of more than two attributes is thus possible. The intensities are read after the first 10 seconds and then every 20 seconds over a period of 70 seconds. The data produced are analysed by means of Compusense® five and represented graphically as a time-intensity curve.

In order to show the astringency-masking effect of L-lactic acid L-menthyl ester (Frescolat ML), the panel was trained inter alia with an aqueous test solution comprising 750 mg/kg of epigallocatechin gallate and 125 mg/kg of ascorbic acid. The panellists were asked to evaluate the test solution in respect of its bitterness and astringency using the above-described method. In a subsequent test, the two descriptors were evaluated on the one hand for the above-described test solution and on the other hand for the test solution plus 300 µg/kg of Frescolat ML. The results of both time-intensity curves were evaluated statistically and compared with one another in order to determine an astringency-masking effect of Frescolat® ML. The test was carried out in triplicate, and the mean values of the astringency reduction are shown in Table 1. For the significance calculation, the Student t-test, duplicated with paired random samples, was used.

TABLE 1

Astringency reduction of 750 mg/kg of EGCG (+125 mg/kg of ascorbic acid) after addition of 300 µg/kg of L-lactic acid L-menthyl ester (Frescolat ® ML), mean value from 2 repetitions

| Time (sec.) | Astringency without Frescolat ML | Astringency with Frescolat ML | Reduction (%) |
| --- | --- | --- | --- |
| 0 | 4.84 | 4.81 | −0.49 |
| 10 | 4.80 | 4.11 | −14.29 |
| 30 | 4.26 | 3.38 | −20.58* |
| 50 | 3.32 | 2.58 | −22.24* |
| 70 | 2.49 | 2.04 | −17.82 |

*significant ($p < 0.1$)

Application Example 1

Various liquid flavour compositions are given in Table 2. The substances or solutions were mixed in the ratios indicated below and then taken up in propylene glycol or ethanol, dissolved completely by gentle heating and mixed homogeneously.

TABLE 2

Formulation examples

| Ingredient | Preparation (amount used in wt. %) | | | | | | | |
| --- | --- | --- | --- | --- | --- | --- | --- | --- |
| | A | B | C | D | E | F | G | H |
| Frescolat ® ML | 1 | 0.6 | 1 | 0.55 | 1.95 | 1 | 0.25 | 1.6 |
| Hesperetin | 2 | — | — | 2 | — | — | — | — |
| Symrise sugar flavour in 1,2-propylene glycol | 1.5 | 4 | — | — | 2 | — | 0.3 | — |
| Symrise milk flavour in 1,2-propylene glycol | — | — | — | 4 | — | — | — | — |
| Symrise cream flavour in 1,2-propylene glycol | — | — | 3 | 0.3 | 0.5 | 5 | 1 | 2.5 |
| 1,2-Propylene glycol | ad 100 | — | ad 100 | ad 100 | ad 100 | ad 100 | — | ad 100 |
| Ethanol | — | ad 100 | — | — | — | — | ad 100 | — |

Application Example 2

Various dry flavour compositions are given in Table 3. The substances were mixed in the ratios indicated below and mixed homogeneously with the solid carriers.

TABLE 3

Formulation examples

| Ingredient | A | B | C | D | E | F | G | H |
|---|---|---|---|---|---|---|---|---|
| Frescolat ® ML | 25 | 15 | 0.5 | 1 | 1 | 0.25 | 1.2 | 6 |
| Approx. 10 wt. % pellitorine in solution 1,2-propylene glycol | — | — | — | — | — | — | — | 10 |
| Approx. 10 wt. % homo-eriodictiol spray-dried | — | — | 35 | 50 | 45 | 15 | 13 | 20 |
| Approx. 10 wt. % hesperetin spray-dried | — | — | — | — | 10 | 10 | 6 | — |
| Symrise rounding-out flavour for tea spray-dried | — | — | 1 | — | 30 | 5 | — | — |
| Symrise sugar flavour in triacetin | 8 | 5 | 0.5 | — | — | — | — | — |
| Symrise vanilla spray-dried | — | — | — | — | — | — | 3 | 10 |
| Dextrose anhydrous | — | ad 100 | — | — | — | ad 100 | — | — |
| Maltodextrin | ad 100 | — | ad 100 | ad 100 | ad 100 | — | ad 100 | ad 100 |

Application Example 3

Various spray-dried flavour compositions in the form of semi-finished products for the flavouring of ready-to-use products are given in Table 4. The drinking water was placed in a container, and the maltodextrin and the gum arabic were dissolved therein. Constituents were then emulsified into the carrier solution described below using a mixer (Turrax). The temperature of the resulting mixture was not to exceed 30° C. The mixture was then spray dried (desired temperature inlet: 185-195° C., desired temperature outlet: 70-75° C.). Spray-dried preparations comprising other flavour compositions according to the invention can also be prepared analogously.

TABLE 4

Formulation examples

| Ingredient | A | B | C | D | E | F |
|---|---|---|---|---|---|---|
| Maltodextrin from wheat | 24.3 | 24.3 | 24.3 | 24.3 | 24.3 | 24.3 |
| Gum arabic | 6.1 | 6.1 | 6.1 | 6.1 | 6.1 | 6.1 |
| Frescolat ® ML | 0.1 | 0.08 | 0.04 | 0.06 | 0.1 | 0.1 |
| Symrise sugar flavour in triacetin | — | 0.5 | 0.2 | — | 0.1 | — |
| Symrise cream flavour in triacetin | — | — | — | 0.05 | 0.05 | — |
| Symrise milk flavour in triacetin | — | — | — | — | — | 0.1 |
| Drinking water | ad 100 | ad 100 | ad 100 | ad 100 | ad 100 | ad 100 |

TABLE 5

Formulation examples

| Ingredient | A | B | C | D |
|---|---|---|---|---|
| Saccharin | 1.50 | 1.50 | 1.50 | 1.50 |
| Flavour composition according to Application Example 2B | — | 1.7 | — | 0.6 |
| Flavour composition according to Application Example 2A | — | — | — | 1.00 |
| Flavour composition according to Application Example 3B | — | — | 1.00 | — |
| Sorbitol | ad 100 | ad 100 | ad 100 | ad 100 |

Application Example 4

Flavour mixtures for reducing the unpleasant taste impressions in a sweetener mixture for sweetening cocoa-, coffee- or tea-containing drinks are given in Table 5. Preparations A to D were added in an amount of 1% to black coffee (freshly brewed). Preparations B, C and D are according to the invention, A is for comparison purposes. Compared with preparation A (comparison), the astringency and long-lasting sweetness were reduced in preparations B to D. The metallic notes were additionally reduced. Preparation D additionally had a more sucrose-typical taste.

Application Example 5

Examples of the use of lactic acid 1-menthyl ester in a sweetener mixture for sweetening reduced-fat, low-fat or fat-free dairy products in order to reduce the unpleasant taste impressions are given in Table 6. Preparations A to D were added in an amount of 1% to black coffee (freshly brewed). Preparations B, C and D are according to the invention, A is for comparison purposes. The flavour compositions and the sweeteners were stirred into neutral yogurt containing 0.1% fat. The mixtures require a maturing time of 3 days. Compared with preparation A (comparison), the astringency and long-lasting sweetness were reduced in preparations B to D. The metallic notes were additionally reduced. A significantly greater sensation of fullness in the mouth (reminiscent of sucrose) was achieved with preparation C.

TABLE 6

Formulation examples

| Ingredient | Preparation (amounts in wt. %) | | | |
|---|---|---|---|---|
| | A | B | C | D |
| Flavour composition according to Application Example 1E | — | 0.03 | — | — |
| Flavour composition according to Application Example 1A | — | — | — | 0.08 |
| Flavour composition according to Application Example 1H | — | — | 0.03 | — |
| Acesulfame K | 0.01 | 0.01 | 0.01 | 0.01 |
| Aspartame | 0.02 | 0.02 | 0.02 | 0.02 |
| Natural yogurt, 0.1% fat | ad 100 | ad 100 | ad 100 | ad 100 |

Application Example 6

Examples of the use of lactic acid 1-menthyl ester in a soy milk drink are given in Table 7. Preparations B to H are according to the invention, A is for comparison purposes. The flavour compositions were mixed with the neutral soy milk. The mixtures required a maturing time of 5 to 6 days. Compared with preparation A (comparison), the astringency of the soy milk was reduced in preparations B to H. The sensation of fullness of the soy milk in the mouth was improved significantly and the soybean notes were reduced in preparations B to D and G+H. In addition to the astringency, the bitterness of the soy milk in particular was reduced in preparations E and F.

TABLE 7

Formulation examples

| Ingredient | Preparation (amounts in wt. %) | | | | | | | |
|---|---|---|---|---|---|---|---|---|
| | A | B | C | D | E | F | G | H |
| Flavour composition according to Application Example 3A | 0.015 | — | — | — | — | — | — | — |
| Flavour composition according to Application Example 1G | — | — | 0.1 | — | — | — | — | — |
| Flavour composition according to Application Example 1F | — | 0.04 | — | — | — | — | — | — |
| Flavour composition according to Application Example 1C | — | — | — | 0.01 | — | — | 0.005 | — |
| Flavour composition according to Application Example 1A | — | — | — | — | — | 0.1 | — | — |
| Flavour composition according to Application Example 1D | — | — | — | — | 0.15 | — | 0.1 | — |
| Flavour composition according to Application Example 3E | — | — | — | — | — | — | — | 0.015 |
| Soy milk, without additives (local supermarket) | ad 100 | ad 100 | ad 100 | ad 100 | ad 100 | ad 100 | ad 100 | ad 100 |

Application Example 7

An example of the use of lactic acid 1-menthyl ester in a soy drink in combination with γ-aminobutyric acid is given in Table 8. γ-Aminobutyric acid was pre-dissolved in water and added, together with a flavour mixture according to the invention, to a soy milk from a local supermarket. The mixture, together with the milk flavour, was stirred in a glass beaker. Compared with Application Example 6 B, the astringency was reduced significantly, the soy milk acquires a very neutral freshness.

TABLE 8

Formulation example

| Ingredient | Amount used in wt. % |
|---|---|
| Soy milk, without additives (local supermarket) | 99.76 |
| Flavour composition according to Application Example 1F | 0.04 |
| 1% γ-aminobutyric acid in water | 0.2 |

Application Example 8

Examples of the use of lactic acid 1-menthyl ester in a soy-fruit drink are given in Table 9. Preparations B to D are according to the invention, A is for comparison purposes. The flavour compositions were mixed with the remaining ingredients. The mixture was homogenised and then pasteurised (15 minutes at 80-85° C.). Compared with preparation A (comparison), the astringency and the soybean notes were reduced in preparations A to D. In preparation B, the bitterness was additionally reduced significantly. All the samples had a markedly more fruity taste.

TABLE 9

Formulation examples

| Ingredient | Preparation (amounts in wt. %) | | | |
|---|---|---|---|---|
| | A | B | C | D |
| Flavour composition according to Application Example 1D | — | 0.12 | 0.1 | — |
| Flavour composition according to Application Example 1A | — | — | — | 0.08 |

TABLE 9-continued

Formulation examples

| Ingredient | Preparation (amounts in wt. %) | | | |
|---|---|---|---|---|
| | A | B | C | D |
| Flavour composition according to Application Example 1C | — | — | 0.003 | — |
| Sweetener mix | 0.03 | 0.03 | 0.03 | 0.03 |
| Sugar | 5 | 5 | 5 | 5 |
| Fruit juice mix from fruit juice concentrates | 50 | 50 | 50 | 50 |
| Water | ad 100 | ad 100 | ad 100 | ad 100 |
| Soy powder | 5 | 5 | 5 | 5 |

Application Example 9

Examples of the use of lactic acid 1-menthyl ester in a soy ice-cream are given in Table 10. Preparations B to D are according to the invention, A is for comparison purposes. The flavour compositions are mixed with the ice-cream mix. The mass is then frozen in the freezer turned up by 100%, and stored at −25° C. Compared with preparation A (comparison), the soybean notes were reduced significantly in preparations B to D.

TABLE 10

Formulation examples

| Ingredient | Preparation (amounts in wt. %) | | | |
|---|---|---|---|---|
| | A | B | C | D |
| Flavour composition according to Application Example 1F | — | 0.06 | — | — |
| Flavour composition according to Application Example 1G | — | — | — | 0.12 |
| Flavour composition according to Application Example 1C | — | — | 0.014 | — |
| Soy ice-cream mix (with 12% saccharose, 8% glucofructose syrup, 3% soy powder, 4.5% fat) | ad 100 | ad 100 | ad 100 | ad 100 |

Application Example 10

Examples of the use of lactic acid 1-menthyl ester in a low-fat yogurt are given in Table 11. Preparations B to D are according to the invention, A is for comparison purposes. The flavour compositions and the sucrose are stirred into the neutral yogurt having a fat content of 0.1%. The mixtures require a maturing time of 3 days. Compared with preparation A (comparison), the astringency was reduced in preparations B to D. In addition, the acidity of the yogurt was reduced. In preparation D, a significantly greater sensation of fullness in the mouth was achieved.

TABLE 11

Formulation examples

| Ingredient | Preparation (amounts in wt. %) | | | |
|---|---|---|---|---|
| | A | B | C | D |
| Flavour composition according to Application Example 1F | — | 0.03 | — | — |
| Flavour composition according to Application Example 1G | — | — | — | 0.1 |

TABLE 11-continued

Formulation examples

| Ingredient | Preparation (amounts in wt. %) | | | |
|---|---|---|---|---|
| | A | B | C | D |
| Flavour composition according to Application Example 3F | — | — | 0.015 | — |
| Sucrose | 5 | 5 | 5 | 5 |
| Natural yogurt, 0.1% fat | ad 100 | ad 100 | ad 100 | ad 100 |

Application Example 11

An example of the use of lactic acid 1-menthyl ester in a reduced-fat mayonnaise is given in Table 12. Compared with reduced-fat mayonnaise without flavour composition, the astringency was improved, the preparation acquired a better sensation in the mouth/oiliness.

TABLE 12

Formulation example

| Ingredient | Amount used in wt. % |
|---|---|
| Reduced-fat mayonnaise | 99.93 |
| Flavour composition according to Application Example 1F | 0.07 |

Application Example 12

Examples of the use of lactic acid 1-menthyl ester in a green tea preparation are given in Table 13. The green tea extract, acid and sweetener mixture as well as the flavour compositions were dissolved in water at 80° and filled into bottles. Compared with the control green tea preparation (without flavour composition), the astringency was reduced. The bitterness was additionally reduced in particular in preparation B; preparation B exhibited significantly fuller sweetness.

TABLE 13

Formulation examples

| Ingredient | Amount used in wt. % | |
|---|---|---|
| | A | B |
| Green tea extract, approx. 16% catechin content | 0.25 | 0.25 |
| Flavour composition according to Application Example 2D | 0.1 | — |
| Flavour composition according to Application Example 2E | — | 0.1 |
| Sweetener mixture (aspartame, sucralose 1:1) | 0.01 | 0.01 |
| Malic acid, citric acid | 0.1 | 0.1 |
| Demineralised water | ad 100 | ad 100 |

Application Example 13

Examples of the use of lactic acid 1-menthyl ester in various tea preparations are given in Table 14. Tea leaves and the semi-finished products were mixed and packed in filter bags. For the tasting, 100 to 250 ml of boiling water were added to the tea bag and left to infuse for 2 to 5 minutes.

TABLE 14

Formulation examples

| Ingredient | Amount used in wt. % | | |
|---|---|---|---|
| | A | B | C |
| Black tea, Ceylon, leaves | 94 | — | — |
| Green tea, China, leaves | — | 92 | — |
| Mate tea, Peru, leaves | — | — | 95 |
| Semi-finished product A from Example 3 | 6 | — | — |
| Semi-finished product B from Example 3 | — | 8 | — |
| Semi-finished product C from Example 3 | — | — | 5 |

Application Example 14

Examples of the use of lactic acid 1-menthyl ester in further tea preparations are given in Table 15. Tea leaves and the semi-finished products were mixed and packed into filter bags. For the tasting, 100 to 250 ml of boiling water are added to the tea bag and left to infuse for 2 to 5 minutes.

TABLE 15

Formulation examples

| Ingredient | Amount used in wt. % | |
|---|---|---|
| | A | B |
| Black tea, Ceylon, leaves | 94 | — |
| Green tea, Japan Sencha, leaves | — | 95 |
| Semi-finished product A from Example 2 | 3 | — |
| Semi-finished product C from Example 2 | 3 | 5 |

Application Example 15

Examples of the use of lactic acid 1-menthyl ester in iced tea preparations based on black tea are given in Table 16.

TABLE 16

Formulation examples

| Ingredient | Amount used in wt. % | |
|---|---|---|
| | A | B |
| Black tea, Assam, leaves | 1.4 | 1.4 |
| Water | ad 100 | ad 100 |
| Natural peach flavour | 0.65 | 0.65 |
| Sucrose | 7 | 7 |
| Citric acid (crystalline) | 1.2 | 1.2 |
| Ascorbic acid | 0.2 | 0.2 |
| Frescolat ® ML | 0.00003 | — |
| Homoeriodictyol (10% in ethanol) | 0.01 | — |
| Matairesinol (10% in ethanol) | — | 0.01 |

Application Example 16

Examples of the use of lactic acid 1-menthyl ester in reduced-calorie iced tea preparations based on green tea are given in Table 17.

TABLE 17

Formulation examples

| Ingredient | Amount used in wt. % | |
|---|---|---|
| | A | B |
| Green tea extract, catechin content 10 wt. % | 1.4 | 1.2 |
| Water | ad 100 | ad 100 |
| Flavour lemon type | 0.65 | 0.65 |
| Sucrose | 3.45 | 3.45 |
| Saccharin, sodium salt | 0.1 | — |
| Rebaudioside A | — | 0.02 |
| Citric acid (crystalline) | 1.2 | 1.2 |
| Ascorbic acid | 0.2 | 0.2 |
| Frescolat ® ML | 0.00005 | 0.00003 |

Application Example 17

Examples of the use of lactic acid 1-menthyl ester in reduced-calorie iced tea preparations based on black tea are given in Table 18.

TABLE 18

Formulation examples

| Ingredient | Amount used in wt. % | |
|---|---|---|
| | A | B |
| Black tea extract | 1.4 | 1.4 |
| Water | Ad 100 | Ad 100 |
| Saccharin | 0.035 | 0.035 |
| Flavour lemon type | 0.65 | 0.65 |
| Citric acid (crystalline) | 1.2 | 1.2 |
| Ascorbic acid | 0.2 | 0.2 |
| Frescolat ® ML | 0.00005 | 0.00004 |
| Eriodictyol (10% in ethanol) | — | 0.05 |
| Black tea extract | 1.4 | 1.4 |

Application Example 18

An example of the use of lactic acid 1-menthyl ester in bitter chocolate is given in Table 19. The ingredients were incorporated into the chocolate, which had been melted at 40° C., and the liquid mass was poured into a tablet mould and cooled according to the tempering process known to the person skilled in the art, edible chocolate being obtained. The chocolate so prepared was described by the trained experts as being less bitter, less astringent and, overall, more rounded.

TABLE 19

Formulation example

| Ingredient | Amount used in wt. % |
|---|---|
| Bitter chocolate, min. 85% cocoa (commercial product) | 99.7 |
| Flavour composition according to Application Example 2G | 0.3 |

The invention claimed is:

1. A preparation for oral consumption, comprising
(a) a lactic acid 1-menthyl ester of formula (I)

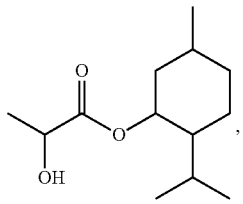

its stereoisomers or mixtures thereof; and
(b) at least one substance having an unpleasant bitter, astringent and/or metallic taste or after-taste;
wherein the lactic acid menthyl ester is present in an amount effective to reduce or mask the unpleasant taste or after-taste of the substance, but at a concentration insufficient to cause a perceptible physiological cooling effect.

2. The preparation according to claim 1, comprising as component (b), substances selected from the group consisting of xanthine alkaloids, xanthines, alkaloids, phenolic glycosides, flavonoid glycosides, chalcones, chalcone glycosides, dihydrochalcone glycosides, hydrolysable tannins, non-hydrolysable tannins, flavones and glycosides thereof, other polyphenols, terpenoid bitter substances, absinthe from wormwood, amarogentin from gentian, metal salts, vitamins, denatonium salts, sucralose octaacetate, urea, unsaturated fatty acids, amino acids, peptides and mixtures thereof.

3. The preparation according to claim 1, comprising as component (b), substances selected from the group consisting of catechins, proanthocyanidins, caffeine, theobromine, naringin, sweeteners and mixtures thereof.

4. The preparation according to claim 1, further comprising flavourings selected from the group consisting of alcohols, aldehydes, ketones, organic acids, esters, lactones, sulfur components, acetals, furans, pyrans and pyrazines and mixtures thereof.

5. The preparation according to claim 4, wherein the flavourings are selected from the group consisting of diacetyl, acetoin, benzaldehyde, furaneol, heliotropin, vanillin, ethylvanillin, ethylvanillin isobutyrate (=3-ethoxy-4-isobutyryloxybenzaldehyde), 2,5-dimethyl-4-hydroxy-3 (2H)-furanone and derivatives thereof, maltol and maltol derivatives, coumarin and coumarin derivatives, gamma-lactones, delta-lactones, methyl sorbate, divanillin, 4-hydroxy-2(or 5)-ethyl-5(or 2)-methyl-3 (2H)furanone, 2-hydroxy-3-methyl-2-cyclopentenone, 3-hydroxy-4,5-dimethyl-2(5H)-furanone, acetic acid isoamyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl 3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde and mixtures thereof.

6. The preparation according to claim 4, wherein the flavourings are selected form the group consisting of homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), ethylmaltol, gamma-undecalactone, gamma-nonalactone, gamma-decalactone, 4-methyldeltadecalactone, massoilactone, deltadecalactone and tuberolactone.

7. The preparation according to claim 1, wherein said preparation is one of foodstuffs, oral and teeth cleaning and care agents, or pharmaceutical preparations.

8. The preparation according to claim 1, wherein said preparation is one of baked goods, confectionery, alcoholic or non-alcoholic drinks, refreshment drinks, nectars, spritzers, fruit and vegetable juices, fruit or vegetable juice preparations, instant drinks, meat products, eggs or egg products, cereal products, dairy products, products made from soy protein or other soybean fractions, products made from other vegetable protein sources, fruit preparations, vegetable preparations, snack articles, fat- and oil-based products or emulsions thereof, other ready meals and soups, spices, spice mixtures, toothpastes, mouthwashes, cold remedies or active ingredient capsules.

9. The preparation according to claim 8, wherein said preparation is spice mixture which is a seasoning.

10. The preparation according to claim 1, wherein the total amount of components (a) and (b), based on ready-for-use end products, is from 0.001 to 1 wt. %.

11. A method of masking unpleasant taste in a preparation for oral consumption, comprising adding to said preparation a lactic acid 1-menthyl ester of formula (I)

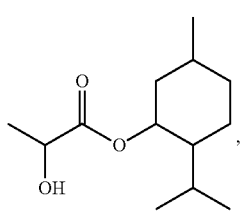

its stereoisomers or mixtures thereof, wherein the preparation comprises at least one substance having an unpleasant bitter, astringent and/or metallic taste or aftertaste, and
wherein the lactic acid menthol ester is added in an amount effective to reduce or mask the unpleasant taste or aftertaste of the substance, but at a concentration insufficient to cause a perceptible physiological cooling effect.

* * * * *